(12) United States Patent
Teoh

(10) Patent No.: US 9,795,766 B2
(45) Date of Patent: Oct. 24, 2017

(54) CATHETER ASSEMBLY BLOOD CONTROL DEVICE AND RELATED METHODS

(71) Applicant: B. BRAUN MELSUNGEN AG, Melsungen (DE)

(72) Inventor: Teng Sun Teoh, Penang (MY)

(73) Assignee: B. Braun Melsungen AG, Melsungen (DE)

(*) Notice: Subject to any disclaimer, the term of this patent is extended or adjusted under 35 U.S.C. 154(b) by 195 days.

(21) Appl. No.: 14/550,448

(22) Filed: Nov. 21, 2014

(65) Prior Publication Data
US 2015/0151084 A1    Jun. 4, 2015

Related U.S. Application Data

(60) Provisional application No. 61/911,944, filed on Dec. 4, 2013.

(51) Int. Cl.
*A61M 25/06* (2006.01)
*A61M 25/00* (2006.01)
*A61M 39/06* (2006.01)

(52) U.S. Cl.
CPC .... *A61M 25/0606* (2013.01); *A61M 25/0097* (2013.01); *A61M 39/0606* (2013.01); *A61M 25/0693* (2013.01); *A61M 2039/064* (2013.01); *A61M 2039/066* (2013.01)

(58) Field of Classification Search
CPC ...... A61M 2039/064; A61M 2039/066; A61M 25/0097; A61M 25/0606; A61M 25/0693; A61M 39/0606
See application file for complete search history.

(56) References Cited

U.S. PATENT DOCUMENTS

| 5,935,110 A * | 8/1999 | Brimhall ........... A61M 25/0637 604/158 |
| 8,066,675 B2 | 11/2011 | Cindrich et al. |
| 8,814,833 B2 | 8/2014 | Farrell et al. |
| 8,932,259 B2 | 1/2015 | Stout et al. |
| 2007/0191810 A1* | 8/2007 | Kennedy ............... A61M 25/00 604/508 |
| 2010/0204648 A1 | 8/2010 | Stout et al. |
| 2010/0222746 A1* | 9/2010 | Burkholz .......... A61M 25/0606 604/164.08 |

(Continued)

*Primary Examiner* — Quynh-Nhu H Vu
(74) *Attorney, Agent, or Firm* — Klein, O'Neill & Singh, LLP

(57) ABSTRACT

A catheter assembly includes a catheter adapter and an introducer needle. The introducer needle extends through the catheter adapter and through a catheter tube so as to assist placement of the catheter tube into a patient's blood vessel. Blood flashback into the catheter tube and/or catheter adapter through an aperture in a side of the needle indicates when the catheter tube is within the blood vessel. After the catheter tube is placed in the blood vessel, the introducer needle is withdrawn. A primary septum within the catheter adapter blocks blood flow in a proximal direction past the primary septum. A secondary septum proximal the primary septum is biased so as to enter into the aperture in the introducer needle and plug the aperture while the needle is being withdrawn, thus blocking blood flow through the aperture after the aperture is drawn through the primary septum.

14 Claims, 8 Drawing Sheets

(56) References Cited

U.S. PATENT DOCUMENTS

| | | | |
|---|---|---|---|
| 2012/0065612 A1* | 3/2012 | Stout | A61M 25/0606 |
| | | | 604/500 |
| 2012/0296255 A1 | 11/2012 | Feng et al. | |
| 2014/0025042 A1* | 1/2014 | Gregersen | A61M 1/3653 |
| | | | 604/523 |
| 2014/0276435 A1 | 9/2014 | Shaw et al. | |

* cited by examiner

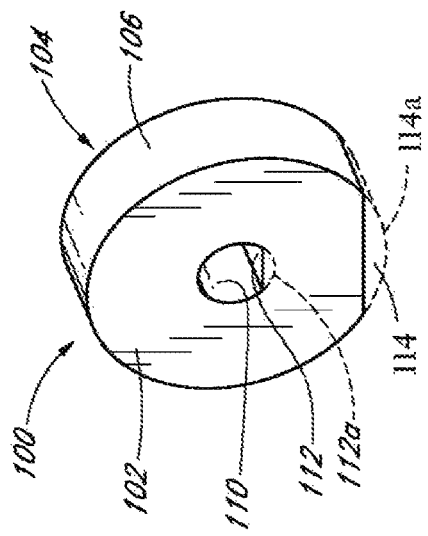
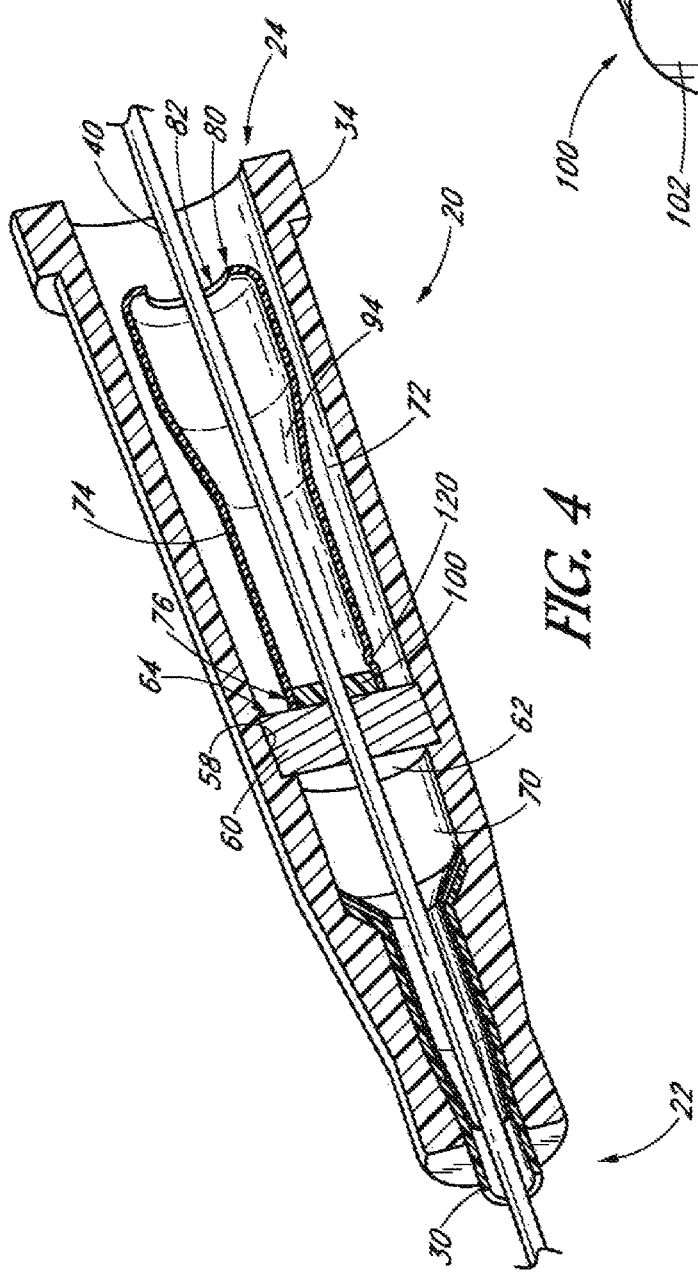
FIG. 4
FIG. 5

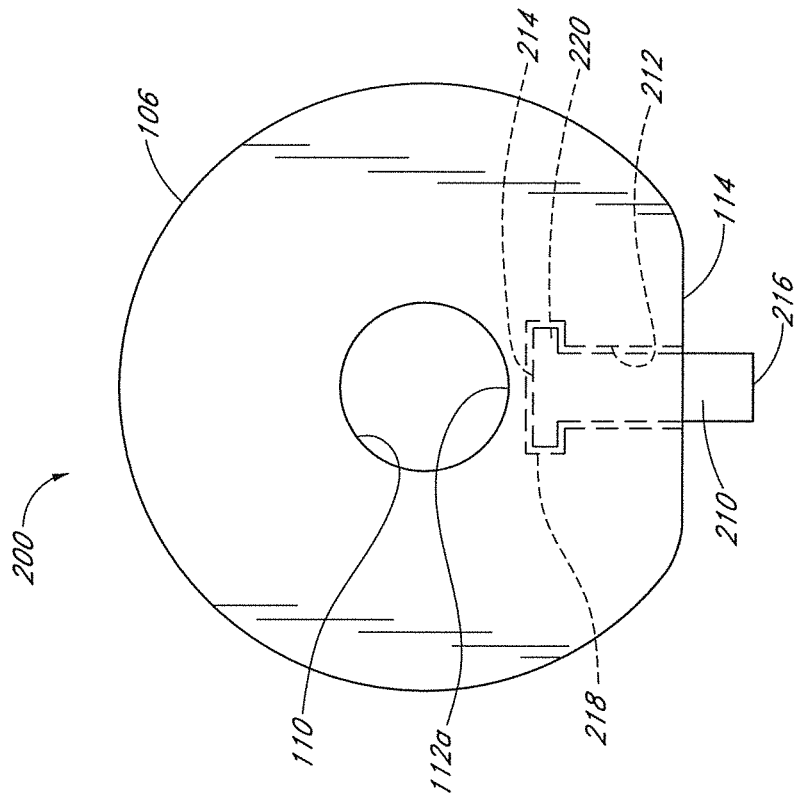
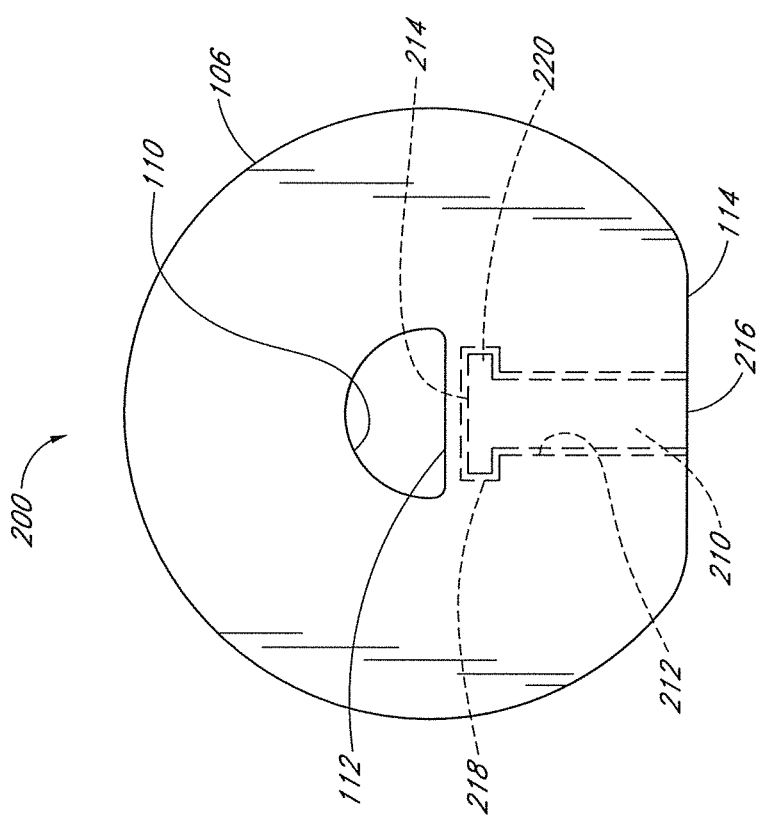

CATHETER ASSEMBLY BLOOD CONTROL DEVICE AND RELATED METHODS

CROSS-REFERENCE TO RELATED APPLICATIONS

The application claims priority to U.S. Provisional Application No. 61/911,944, which was filed on Dec. 4, 2013, the entirety of which is hereby incorporated by reference.

BACKGROUND

The present disclosure relates to the field of infusion devices, and more particularly to peripheral intravenous (IV) catheters.

A catheter assembly for an IV catheter generally includes a flexible catheter or catheter tube coupled to a distal end of a catheter adapter, which is also known as a catheter hub. The catheter adapter retains the catheter tube so that other components can interact with the catheter tube. In order to place the catheter tube in the patient's blood vessel, an introducer needle is coupled to the catheter adapter so that the needle extends through the catheter tube, with the sharp distal tip of the needle positioned just beyond the distal end of the catheter tube. The clinician uses the introducer needle to penetrate the patient's tissue and place the distal end of the catheter tube in a blood vessel.

Once the needle tip and the catheter tube are in the vessel, the clinician typically uses blood flashback to confirm that placement is correct. For example, the introducer needle can have an aperture, formed through its side proximal of its hollow tip. When properly placed in the vasculature of the patient, blood will flow into the tip of the introducer needle and out the needle notch. Typically the needle aperture is positioned within the catheter tube, and blood exiting the aperture will flow through the catheter tube and/or into a viewing portion of the catheter adapter. When the clinician sees the blood flow, the clinician knows that the distal tip of the needle and/or the distal end of the catheter tube is in place in the blood vessel.

During blood flashback, blood may accumulate in the catheter tube and catheter adapter. A septum in the catheter adapter contains the blood in a distal chamber of the catheter adapter. Once it is verified that the catheter tube is correctly placed in the blood vessel, the introducer needle is removed, and a source of IV fluids can be attached to the catheter adapter via a coupler. However, when the introducer needle is being removed there is a risk of blood flowing through the needle and exiting the needle aperture proximal of the septum.

SUMMARY

Accordingly, there is a need in the art for a catheter assembly which prevents or inhibits blood flow out of the aperture as the introducer needle is removed from the catheter tube.

In accordance with an embodiment, the present disclosure provides a catheter assembly, comprising a catheter adapter, a primary septum, an introducer needle and a secondary septum. The catheter adapter defines an internal space. The primary septum is within the internal space, and the primary septum divides the internal space into a distal chamber and a proximal chamber. The introducer needle extends through the primary septum. The introducer needle is hollow and has a distal tip and a notch formed in a side wall of the needle proximal of the distal tip. An aperture through the needle side wall is formed in the notch. The secondary septum is disposed in the proximal chamber. The secondary septum has a needle hole through which the introducer needle extends. The secondary septum is biased inwardly at the needle hole. The needle generally deforms the secondary septum radially outwardly at the needle hole. When the introducer needle is drawn proximally so that the needle notch enters the secondary septum needle hole, a portion of the secondary septum extends into the notch so as to plug the notch aperture.

In some embodiments the secondary septum can be configured so that after the secondary septum engages the needle notch, the secondary septum moves proximally with the needle.

Further embodiments can additionally comprise a detent arranged proximal of the secondary septum in the proximal chamber. The detent is configured to exert a distally-directed force on the secondary septum as the introducer needle is drawn proximally so as to oppose proximal movement of the secondary septum.

In some such embodiments, when the portion of the secondary septum extends into the notch, a distal face of the secondary septum can engage a distal end of the notch so that a portion of a proximally-directed force applied to the introducer needle is communicated to the secondary septum distal face. In additional embodiments, the portion of the proximally-directed force can be greater than the distally-directed force exerted by the detent.

In additional embodiments the secondary septum can be configured so that when the portion of the secondary septum extends into the notch, a corresponding portion along a circumference of the secondary septum moves radially inwardly so that the distally-directed force exerted by the detent is reduced or eliminated.

Some embodiments can additionally comprise a septum activator within the proximal chamber, and the secondary septum can be supported within the septum activator. In some such embodiments, the septum activator can have a proximal opening, and a radius of the proximal opening can be greater than a radius of the secondary septum.

In yet other embodiments, the secondary septum needle hole can be biased inwardly at a flat portion that lies flat when in a relaxed condition, and the needle notch can be aligned with the flat portion.

In still further embodiments, the secondary septum can comprise a rigid latch insert configured to move radially outwardly when the needle hole is radially expanded. In such embodiments, the secondary septum can be supported on a mount, and the mount can comprise a latch receiver configured to selectively receive a distal portion of the rigid latch insert. The latch receiver can have a stop configured to block the distal portion of the latch insert from moving proximal past the stop when the distal portion of the latch insert is received in the latch receiver.

In accordance with another embodiment, the present disclosure provides a medical method. The method initially comprises providing a catheter assembly comprising a catheter adapter defining a distal chamber and a proximal chamber separated by a primary septum. A secondary septum is positioned proximal the primary septum and in the proximal chamber. The catheter adapter has a catheter tube extending distally therefrom, and an introducer needle extends through the secondary septum and the catheter tube. The introducer needle has a notch formed in a side wall. The method additionally comprises pulling the introducer needle proximally relative to the catheter adapter and the secondary septum. A portion of the secondary septum enters the notch when the notch passes through the secondary septum so that the secondary septum plugs an aperture formed in the notch. After the portion of the secondary septum enters the notch, the introducer needle is pulled proximally relative to the catheter adapter, and the secondary septum moves proximally with the introducer needle.

Additional embodiments can additionally comprise a stop structure blocking the secondary septum from moving proximally with the needle prior to the portion of the secondary septum entering the notch. In some such embodiments, a shape of the secondary septum can change sufficiently when the portion of the secondary septum enters the notch so that the stop structure is no longer blocked by the secondary septum.

Yet additional embodiments can additionally comprise maintaining a distal end of the catheter tube in the patient's blood vessel while pulling the introducer needle proximally.

BRIEF DESCRIPTION OF THE DRAWINGS

FIG. 4 is a cutaway view showing a catheter adapter with an introducer needle extending therethrough;

FIG. 5 is a perspective view of a secondary septum for use in the catheter adapter of FIG. 4;

FIG. 8A is a schematic view of an embodiment of a secondary septum arranged in the first configuration;

FIG. 8B shows the secondary septum of FIG. 8A and a second configuration; and

DESCRIPTION

Figure 1:
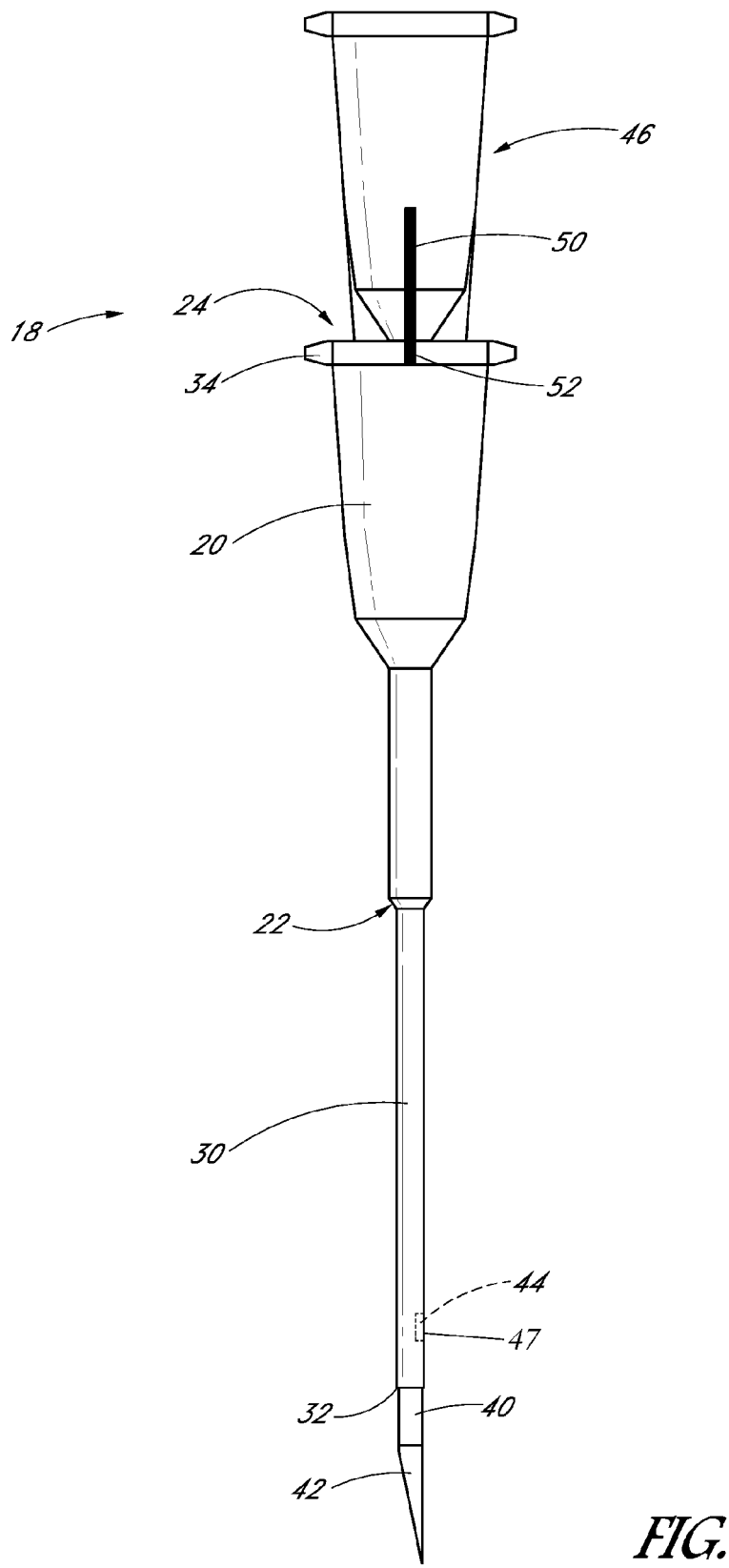
FIG. 1 shows a perspective view of a catheter assembly having features in accordance with the present disclosure.

With initial reference to FIG. 1, an embodiment of a catheter assembly 18 is shown. The catheter assembly 18 includes a catheter adapter 20, also sometimes referred to as a catheter hub, having a distal end 22 and a proximal end 24. A catheter tube 30 extends from the distal end 22 of the adapter and terminates at a catheter distal end 32. A flange or threads 34 at the proximal and 24 of the catheter adapter 20 is configured to releasably accommodate other components, such as a coupler for coupling IV fluid tubing in a luer fit or threaded arrangement.

As shown, an introducer needle 40 has a hollow distal tip 42. In the illustrated embodiment, an outlet aperture 47 in the form of (or as part of) a notch 44 is formed on a side of the introducer needle 40 proximal the distal tip 42. In the illustrated embodiment, the notch 44 is elongated and has a distal end 43 and a proximal end 45. The notch 44 can be formed in various ways, including by crimping the needle and forming an aperture 47 at the notch in part or all of the crimped portion. The needle hub 46 is engaged with the proximal end 24 of the catheter adapter 20. The introducer needle 40 extends from the hub 46 through the catheter adapter 20 and the catheter tube 30 so that its distal tip 42 is disposed just distal of the distal end 32 of the catheter tube 30.

The illustrated needle hub 46 has a fairly simple construction. It is to be understood, however, that in additional embodiments the needle hub can be configured differently and may have additional features such as safety features including a needle tip cover, a spring-loaded needle retractor, or the like.

With continued reference to FIG. 1, a hub marker 50 is formed on the needle hub 46, and an adapter marker 52 is formed on the catheter adapter. When the hub marker 50 and adapter marker 52 are aligned as shown in FIG. 1, the introducer needle 40 is aligned properly for operation in accordance with a preferred embodiment. The markers 50, 52 can be raised (or lowered) portions of the associated component, and/or they can be colored in order to aid visibility. In other examples, the threads or flange 34 can have a notch and the needle hub can have a projection that fits within the notch to angularly align the catheter hub to the needle hub. The notch and the projection can also be reversed.

With reference next to FIGS. 2-5, the catheter adapter 20 defines an internal lumen 56 extending from the proximal end 24 to the distal end 22. A septum seat 58 is formed in an inner wall of the catheter adapter 20. An elastomeric septum 60 preferably is configured to fit in the septum seat 58 so as to sealingly engage the inner wall of the catheter lumen 56 at the septum seat 58. The illustrated septum 60 has a distal face 62 and a proximal face 64. At least one slit 66 is formed through the septum 60 so that the septum 60 can be selectively deformed in order to open the slit and break the seal. Also, preferably the introducer needle 40 can extend through the slit 66, but edges of the slit 66 will engage the outer walls of the needle so as to maintain a full or partial sealing engagement with the needle 40.

As best shown in FIG. 4, a distal chamber 70 is defined within the catheter adapter lumen 56 distal of the septum 60. A proximal chamber 72 is defined proximal of the septum 60.

Figure 2:
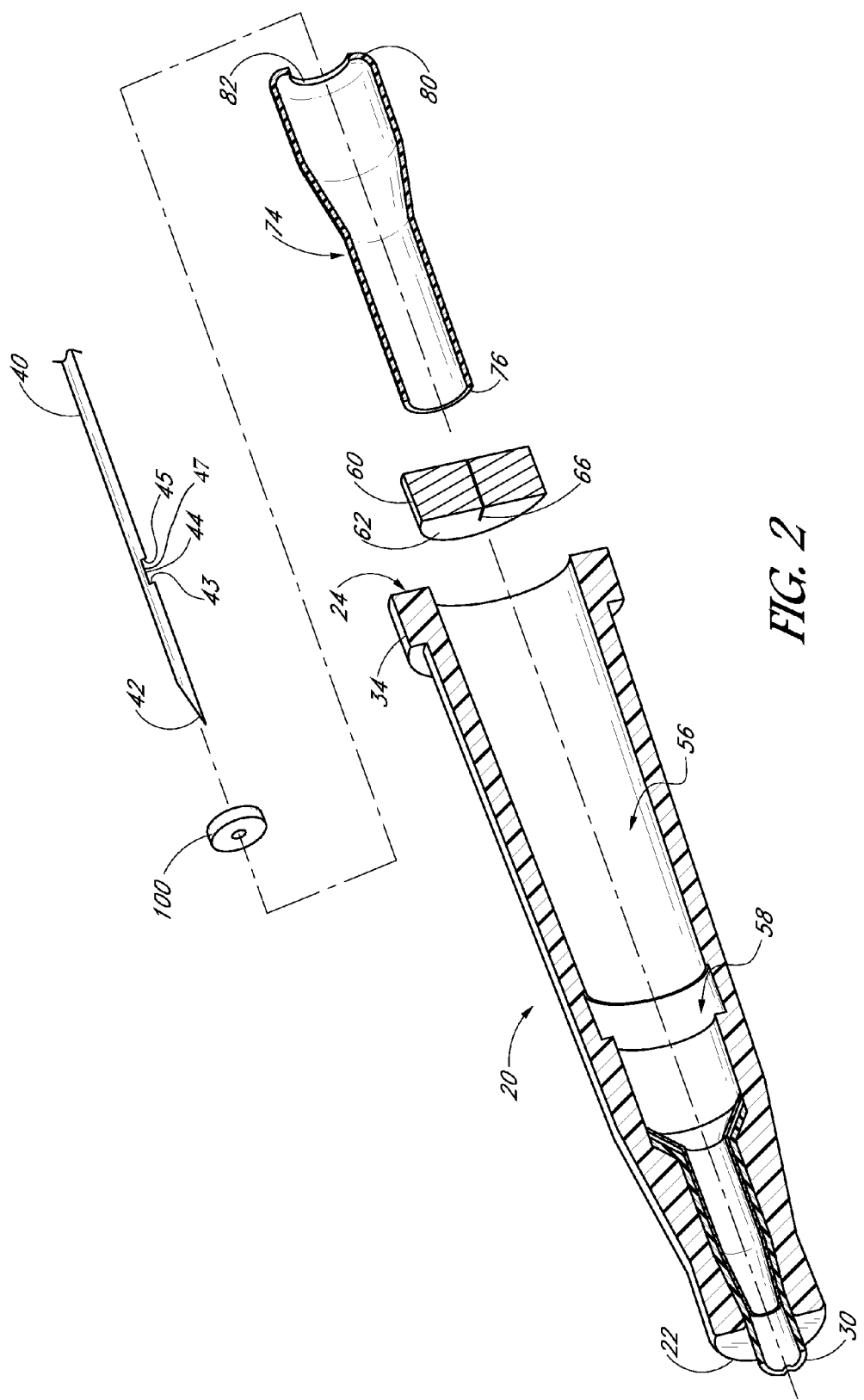
FIG. 2 is an exploded, cutaway view of the catheter assembly of FIG. 1.
Figure 3:
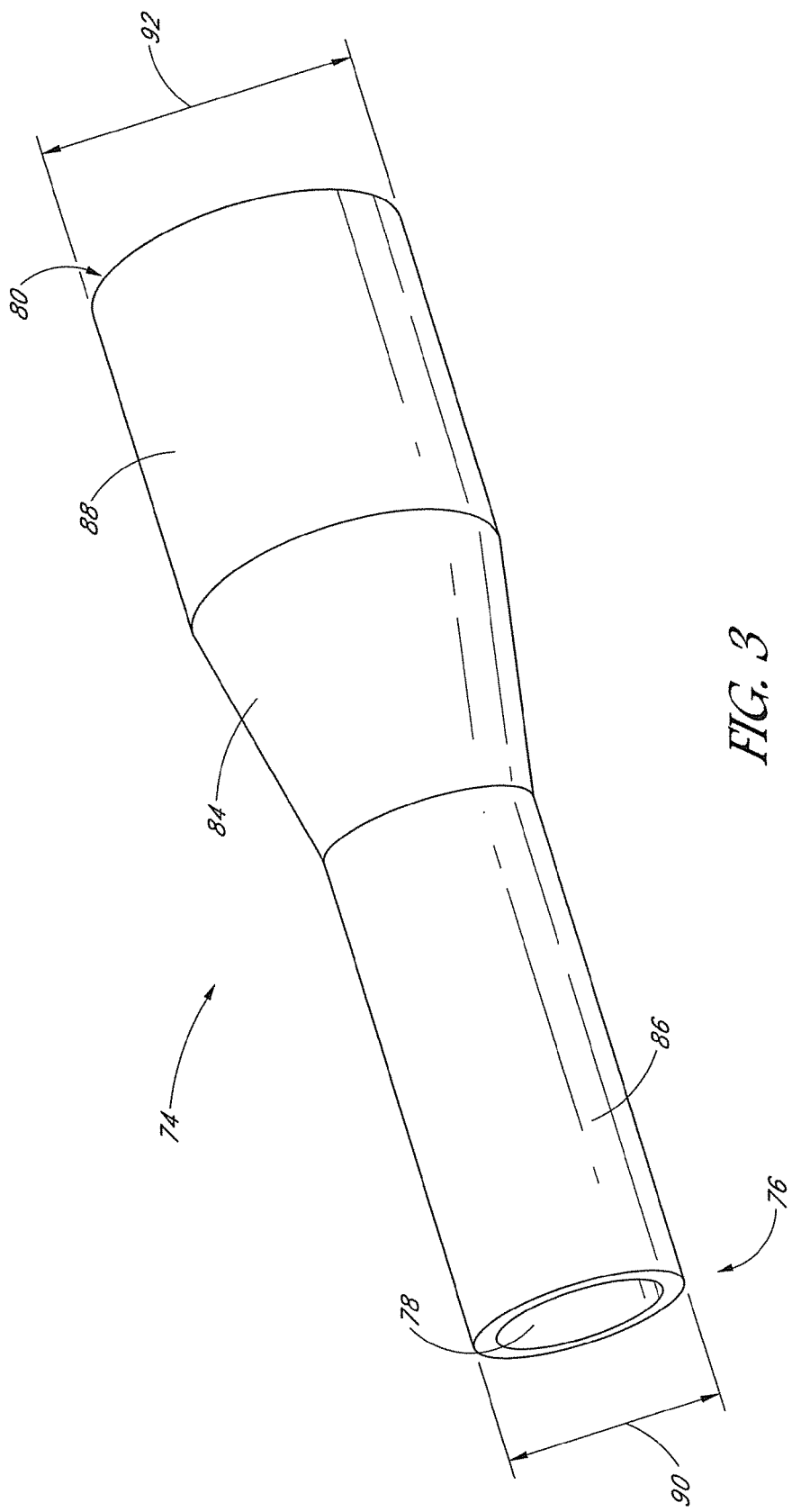
FIG. 3 is a perspective view of a septum activator in accordance with one embodiment.

With continued reference to FIGS. 2-4, a septum activator 74 has a distal end 76 at which a distal opening 78 is formed, and a proximal end 80 at which a proximal opening 82 is formed. The illustrated septum activator 74 has a transition section 84 disposed between the distal section 86 and a proximal section 88. A diameter of the septum activator 74 increases moving proximally through the transition section 84 so that a proximal diameter 92 of the septum activator is greater than a distal diameter 90. An activator lumen 94 is defined within the septum activator.

As best shown in FIG. 4, when the catheter assembly is assembled, the septum activator 74 preferably is disposed within the proximal chamber 72 of the catheter adapter 20 so that the distal end 76 of the activator 74 is adjacent the proximal face 64 of the septum 60, and the introducer needle 40 extends through the activator lumen 94. Although not shown, the septum activator may include guides or fins along an exterior thereof for aligning to the catheter lumen to limit yawing and pitching.

With reference again to FIGS. 2, 4 and 5, an elastomeric secondary septum 100 is arranged at the distal opening 78 of the septum activator 74. With specific reference to FIG. 5, the secondary septum 100 preferably comprises a distal face 102, a proximal face 104 and a circumferential surface 106 extending between the distal and proximal faces 102, 104. A needle hole 110 preferably is formed axially through the secondary septum 100. The illustrated needle hole 110 is generally circular except for an inwardly-biased portion 112. In the illustrated embodiment, the inwardly-biased portion 112 is generally flat when the septum 100 is at rest, and is disposed closer to an axis of the hole 110 than is the rest of the needle hole surface. A recessed portion 114 of the circumferential surface 106 is generally aligned with and radially spaced from the inwardly-biased portion 112.

With continued reference to FIG. 5, when the introducer needle 40 (which typically has a circular cross-sectional shape) extends through the needle hole 110, the inwardly-biased portion 112 is forced radially so as to take on a displaced shape 112a. Similarly, when the inwardly-biased portion 112 is displaced, the recessed portion also takes on a displaced shape 114a so that the radius of the secondary septum 100 in the recessed portion 114 increases when the introducer needle 40 extends through the needle hole 110.

FIG. 4 depicts the catheter adapter 20 with the introducer needle 40 extending therethrough so that the needle extends through the secondary septum 100 needle hole 110, and the recessed portion 114a of the secondary septum 100 is radially expanded. In the illustrated embodiment, a detent or stop 120 is formed in the septum activator 74 just proximal of the secondary septum 100. The illustrated detent 120 is an inwardly-crimped portion of the septum activator 74, which is generally aligned with the position of the recessed portion 114. When the recessed portion is in the expanded configuration 114a, the detent 120 blocks the secondary septum 100 from moving proximally relative to the septum activator 74.

With the catheter assembly 18 assembled as illustrated in FIGS. 1 and 4, the catheter assembly 18 is ready to be placed into a patient's blood vessel. In use, the clinician penetrates the patient's tissue using the distal tip 42 of the needle 40. Once the distal tip 42 is in the blood vessel, blood will flow into the needle 40 at the tip 42 and out the aperture 47 at the notch 44 into the catheter tube 30 and/or catheter adapter 20. More precisely, blood flashback can be expected to at least partially fill the distal chamber 42 of the catheter adapter 20. In some embodiments, air vents may be formed through or around the septum 60 so as to relieve positive air pressure that may tend to resist blood flashback.

Once the catheter tube 30 is properly positioned with its distal end 32 in the patient's blood vessel, the introducer needle 40 should be removed. In a preferred embodiment, prior to such removal, the clinician ensures that the hub marker 50 and adapter marker 52 are aligned so that the introducer needle 40 is positioned with the notch 44 on the same side of the needle as the inwardly-biased portion 112 of the secondary septum 100. As the introducer needle 40 is pulled proximally during withdrawal, the needle will slide through the needle hole 110 of the secondary septum 100. However, since the inwardly-biased portion 112 of the needle hole 110 is in its displaced position, and the recessed portion 114a is correspondingly expanded, the secondary septum 100 is blocked by the detent or stop 120 from being pulled proximally by the needle 40.

Figure 6:
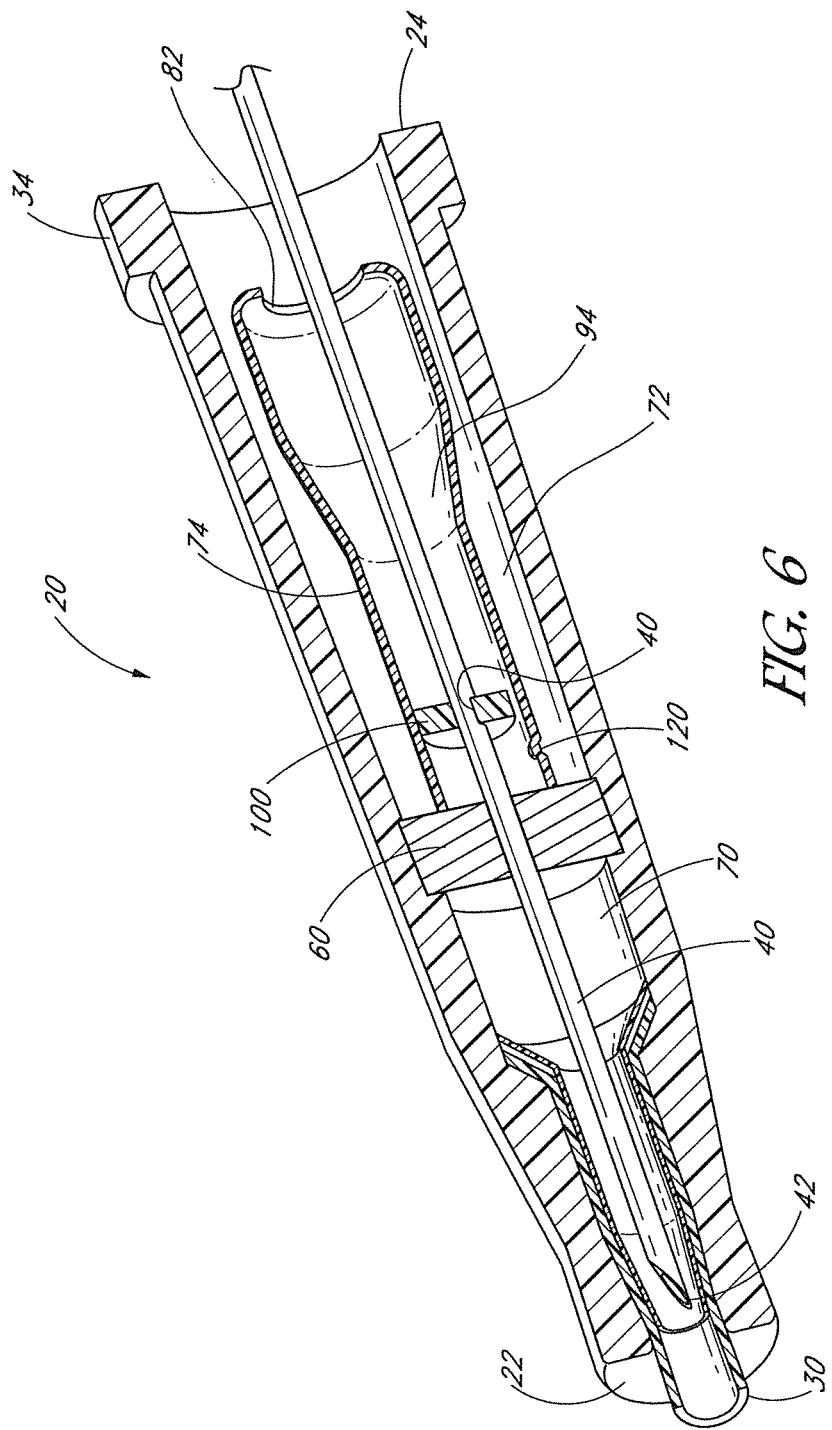
FIG. 6 shows the arrangement of FIG. 4 as an introducer needle is being withdrawn.

With reference next to FIG. 6, eventually the notch 44 of the introducer needle 40 is pulled through the septum 60 and into the needle hole 110 of the secondary septum 100. As noted above, preferably the notch 44 is on the same side of the needle as the biased portion 112. Thus, when the notch 44 passes through the needle hole 110, the inwardly-biased portion 112 will spring into the notch 44. In a preferred embodiment, preferably the thickness of the secondary septum 100 between the distal and proximal faces 102, 104 matches the length of the elongated notch 44 so that when the inwardly-biased portion 112 enters the notch 44, it plugs the notch 44 so that blood is blocked from flowing out of the notch 44. Also, preferably the distal face 102 and proximal face 104 of the secondary septum 100 engage the distal end 43 and proximal end 45, respectively, of the notch 44.

As the inwardly-biased portion 112 of the needle hole 110 moves into the notch 44, the displaced recessed portion 114a moves towards its relaxed state, reducing the effective radius of the secondary septum 100 at the recessed portion 114 so that the recessed portion 114 either clears or can be relatively easily pulled over the detent 120. Also, with the inwardly-biased portion 112 received into the needle notch 44, the needle now has a firm purchase on the secondary septum 100, as the notch distal end 43 is engaged with the distal face 102 of the septum 100. Thus, as the needle 40 continues to be pulled proximally, the secondary septum 100 moves proximally with the needle as depicted in FIG. 6.

Figure 7:
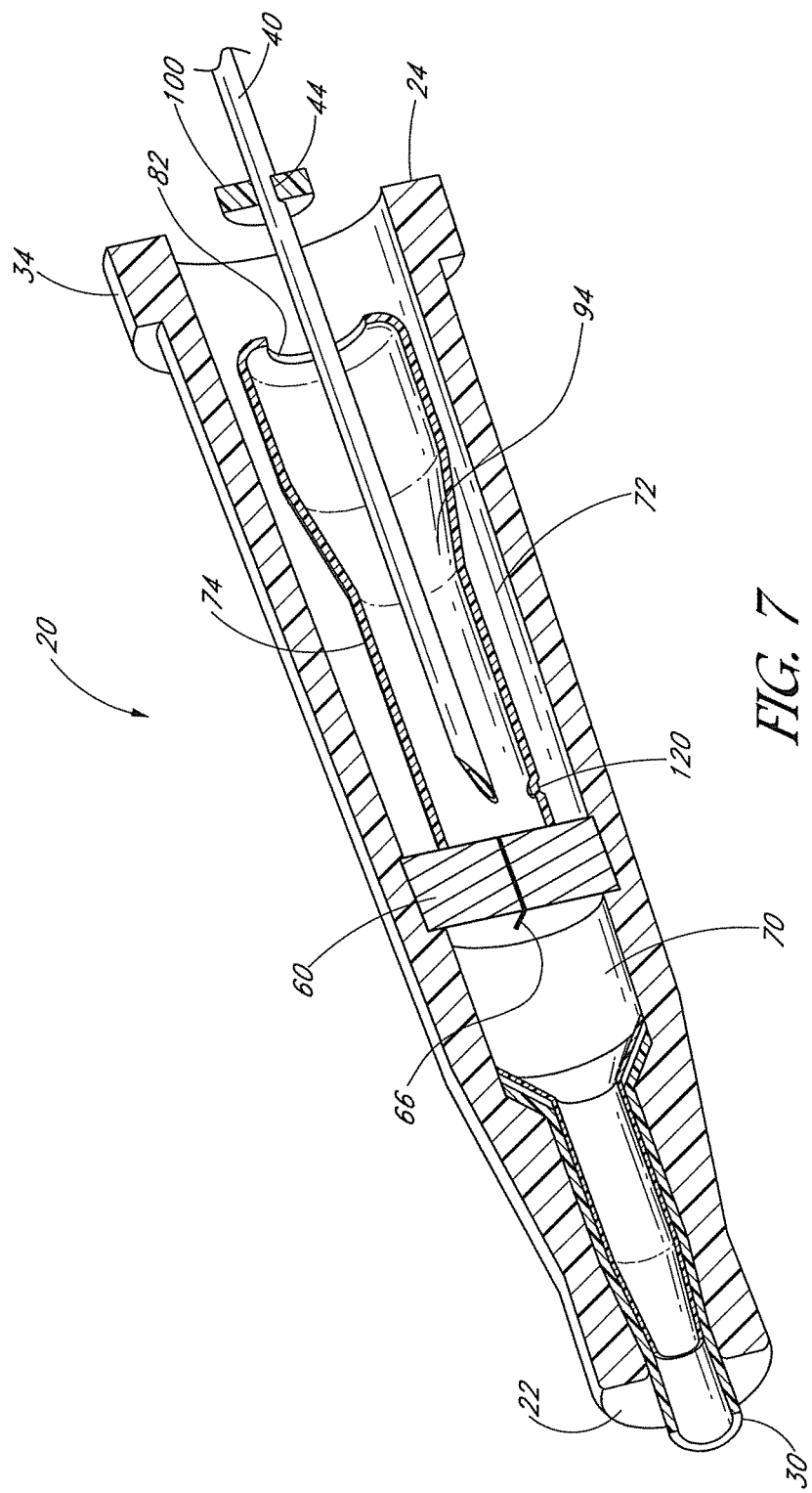
FIG. 7 shows the arrangement of FIG. 4 with the introducer needle further withdrawn.

Preferably, the proximal opening 82 of the septum activator 74 has a diameter greater than the diameter of the secondary septum 100 so that the secondary septum can be completely removed from the catheter adapter with the needle 40 as depicted in FIG. 7. Further, since the secondary septum 100 effectively plugs the needle notch 44 as soon as the needle notch passes through the septum 60 and into the proximal chamber 74 of the catheter adapter 20, the pathway of blood flow into the hollow needle tip 42 and out the needle notch 44 is plugged, and blood is blocked from flowing through the needle into the proximal chamber 72 of the catheter adapter.

In some embodiments, after the introducer needle 40 has been removed, a conduit coupler (not shown) that is connected to a source of IV fluids can be connected to the flange 34 of the catheter adapter 20. During the act of coupling the conduit coupler with the flange 34 a portion of the coupler may push the septum activator 74 distally, deforming the septum 60 so that the slit 66 opens to form one or more fluid pathways through the septum 60. IV fluids can then be delivered into the catheter adapter 20, through the open septum 60 and into the catheter tube 30 for delivery to the patient's blood vessel. Such IV fluids may also flush blood out of the distal chamber 70.

It is to be understood that other embodiments may practice the principles discussed herein while using various structures that may differ from the specifically-illustrated structures. For example, although the illustrated embodiment uses a crimped portion 120 as a detent or stop structure, other structures and configurations can also be employed, such as a ball-and-spring detent, a weak adhesive, a roughened surface, magnets in the catheter adapter body and secondary septum, or the like. Also, rather than having only a portion of the secondary septum needle hole 110 be biased inwardly, the entire needle hole can be biased inwardly so that the secondary septum will be drawn into the needle notch regardless of needle alignment. Further, the periphery of the secondary septum may or may not tend to be expanded by displacement of the needle hole engaging the needle notch. Rather, increased purchase and grip provided to the needle when the secondary septum is drawn into the needle notch may be sufficient to release the secondary septum from the particular stop structure that is employed.

In another embodiment, more than one aperture may be formed through the needle side so that the secondary septum is drawn into the needle at more than one position. In such an embodiment, multiple stop structures may also be employed as desired. In still other embodiments, the needle may be crimped to form one or more notches, and an opening formed at, for example, a distal end of one or each crimp.

With reference next to FIGS. 8A and 8B, another embodiment of a secondary septum 200 is illustrated. This embodiment also employs a needle hole 110 with an inwardly-biased portion 112 and a circumferential surface 106 having a recessed portion 114. Preferably, however, a generally-rigid latch insert 210 is disposed within an insert receiver 212 formed within the septum 200. The latch insert 210 has a proximal end 214 disposed adjacent the inwardly-biased portion 112. A distal end 216 of the latch 210 is generally aligned with the recessed portion 114 when the secondary septum 200 is in a relaxed configuration as illustrated in FIG. 8A. In the illustrated embodiment, the insert receiver cavity 212 includes a retainer portion 218 that is shaped generally complementary to a proximal flange 220 of the latch insert 210 so that the latch insert 210 doesn't fall out of the secondary septum 200.

When the introducer needle extends through the needle hole 110 so as to displace the biased portion 112a, the latch insert 210 is pushed radially so that the distal end 216 extends radially from the recessed portion 114.

Figure 9:
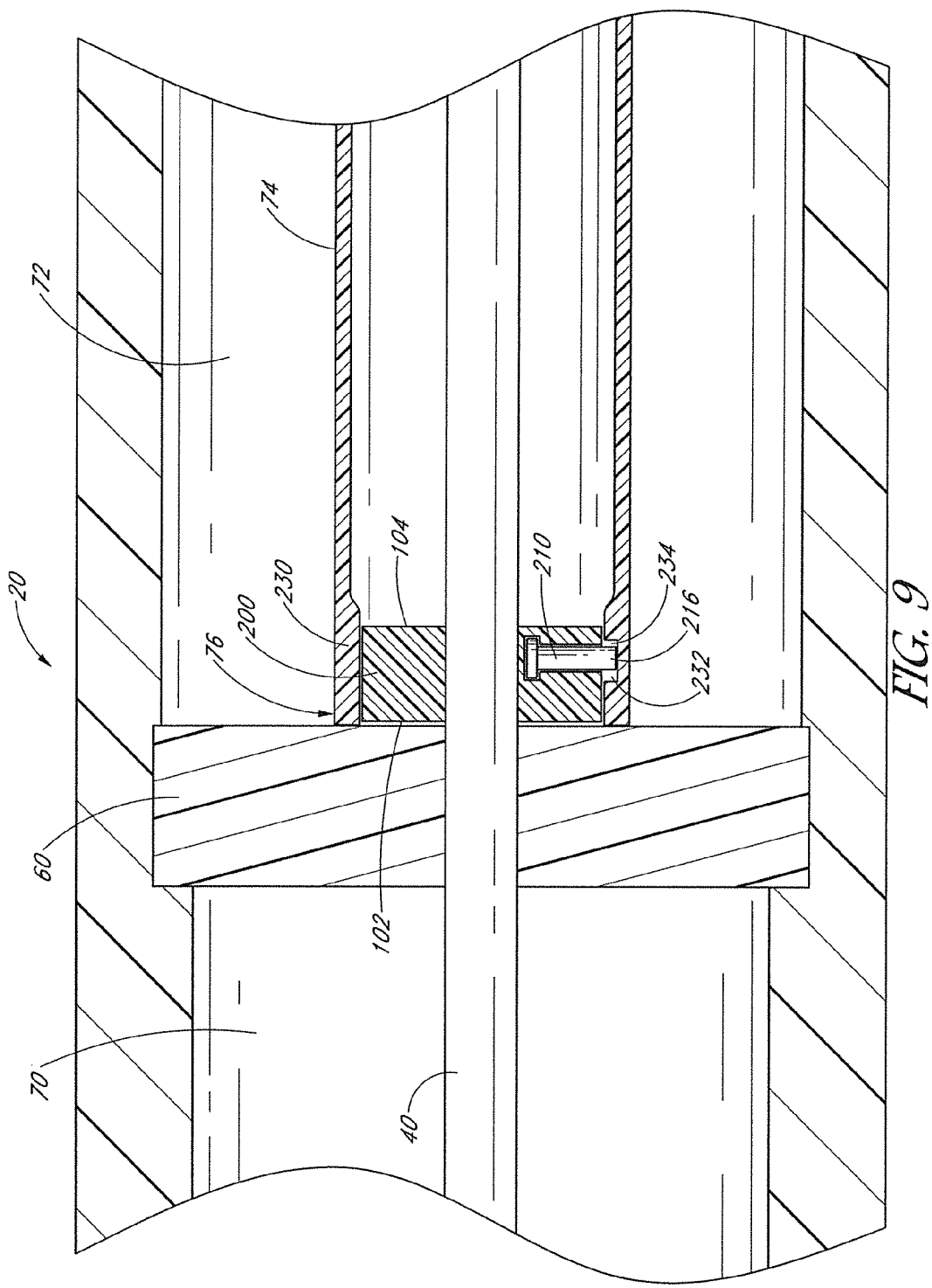
FIG. 9 shows a close up cutaway view of portions of another embodiment of a catheter assembly in accordance with the present disclosure.

With reference next to FIG. 9, in another embodiment, a septum activator 74 is configured with a distal mount portion 230 adjacent its distal end 76. As shown, the secondary septum 200 can be supported at the distal mount portion 230 so that its distal face 102 is adjacent the proximal face 64 of the septum 60. A latch receiver cavity 232 having a stop wall 234 preferably is formed in the distal mount portion 230. The secondary septum 200 is positioned so that when the introducer needle 40 extends through the needle hole 110 the needle hole 110 is expanded, and the latch insert 210 is thus urged radially and the distal end 216 is received in the latch receiver cavity 232. The secondary septum 200 is thus prevented by the stop wall 234 from moving proximally. However, when the introducer needle notch 44 becomes aligned with the biased portion 112, the secondary septum 200 will return toward its relaxed position as shown in FIG. 8A. The distal end 216 of the latch insert 210 will thus be withdrawn from the latch receiver cavity 232 so that the secondary septum 200 will no longer be blocked from moving proximally relative to the activator 74.

With continued reference to FIG. 9, in the illustrated embodiment, an inner diameter of the activator 74 increases immediately proximal to the distal mount portion 230. The increased diameter provides increased space to minimize interference of the activator 74 with the secondary septum as it is drawn proximally.

Although inventive subject matter has been disclosed in the context of certain preferred or illustrated embodiments and examples, it will be understood by those skilled in the art that the inventive subject matter extends beyond the specifically disclosed embodiments to other alternative embodiments and/or uses of the invention and obvious modifications and equivalents thereof. In addition, while a number of variations of the disclosed embodiments have been shown and described in detail, other modifications, which are within the scope of the inventive subject matter, will be readily apparent to those of skill in the art based upon this disclosure. It is also contemplated that various combinations or subcombinations of the specific features and aspects of the disclosed embodiments may be made and still fall within the scope of the inventive subject matter. For example, it is contemplated that additional embodiments can combine structure and principles suggested by, for instance, both FIGS. 4 and 9. Accordingly, it should be understood that various features and aspects of the disclosed embodiments can be combined with or substituted for one another in order to form varying modes of the disclosed inventive subject matter. Thus, it is intended that the scope of the inventive subject matter herein disclosed should not be limited by the particular disclosed embodiments described above, but should be determined only by a fair reading of the claims that follow.

What is claimed is:

1. A catheter assembly, comprising:
   a catheter adapter defining an internal space;
   a primary septum within the internal space, the primary septum dividing the internal space into a distal chamber and a proximal chamber;
   an introducer needle extending through the primary septum, the introducer needle being hollow and having a distal tip, a side wall, a notch formed in the side wall of the introducer needle proximal of the distal tip, and an aperture formed in the notch;
   a secondary septum disposed in the proximal chamber, the secondary septum having an outer circumference and a bore through which the introducer needle extends, the introducer needle generally deforming the secondary septum radially outwardly at the bore;
   wherein when the introducer needle is drawn proximally so that the notch enters the bore of the secondary septum, a portion of the secondary septum extends into the notch so as to plug the aperture at the notch and the portion of the secondary septum that extends into the notch forms a connection with the notch such that the secondary septum is now movable with the introducer needle and relative to the catheter adapter.

2. A catheter assembly as in claim 1, wherein the secondary septum is configured so that after the secondary septum engages the notch, the secondary septum moves proximally with the introducer needle.

3. A catheter assembly as in claim 2 additionally comprising a detent on a septum activator arranged proximal of the secondary septum in the proximal chamber, wherein the detent is configured to exert a distally-directed force on the secondary septum as the introducer needle is drawn proximally so as to oppose proximal movement of the secondary septum.

4. A catheter assembly as in claim 3, wherein when the portion of the secondary septum extends into the notch, a distal face of the secondary septum engages a distal end of the notch so that a portion of a proximally-directed force applied to the introducer needle is communicated to the secondary septum distal face.

5. A catheter assembly as in claim 4, wherein the portion of the proximally-directed force is greater than the distally-directed force exerted by the detent.

6. A catheter assembly as in claim 4, wherein the secondary septum is configured so that when the portion of the secondary septum extends into the notch, a corresponding portion along a circumference of the secondary septum moves radially inwardly so that the distally-directed force exerted by the detent is reduced or eliminated.

7. A catheter assembly as in claim 1 additionally comprising a septum activator within the proximal chamber, and the secondary septum is supported within the septum activator.

8. A catheter assembly as in claim 7, wherein the septum activator has a proximal opening, and a radius of the proximal opening is greater than a radius of the secondary septum.

9. A catheter assembly as in claim 1 wherein the bore of the secondary septum is biased inwardly at a flat portion that lies flat when in a relaxed condition, and wherein the notch is aligned with the flat portion.

10. A catheter assembly, comprising:
a catheter adapter defining an internal space;
a primary septum within the internal space, the primary septum dividing the internal space into a distal chamber and a proximal chamber;
an introducer needle extending through the primary septum, the introducer needle being hollow and having a distal tip, a side wall, a notch formed on the side wall of the introducer needle, and an aperture formed through the notch;
a septum activator disposed in the proximal chamber, the septum activator defining an activator lumen and having a proximal opening;
a secondary septum having a bore through which the introducer needle extends, the secondary septum being removably fixed in the activator lumen of the septum activator when the introducer needle extends through the bore;
wherein when the introducer needle is drawn proximally and the notch passes through the secondary septum, a portion of the secondary septum extends into the notch so as to plug the aperture formed at the notch; and
wherein after the secondary septum engages the notch, the secondary septum is movable relative to the septum activator.

11. A catheter assembly as in claim 10, wherein a size of the secondary septum is smaller than the proximal opening of the septum activator, and the secondary septum is removable through the proximal opening of the septum activator.

12. A catheter assembly as in claim 11, wherein the septum activator has a distal section and a proximal section, a diameter of the proximal section of the septum activator being greater than a diameter of the distal section of the septum activator, and the secondary septum being removably fixed at the distal section of the septum activator.

13. A catheter assembly as in claim 12, wherein the septum activator has a transition section disposed between the distal section and the proximal section.

14. A catheter assembly as in claim 11, wherein the septum activator further comprises a detent formed in the distal section blocking proximal movement of the secondary septum past the detent.

* * * * *